United States Patent
Doshi

(10) Patent No.: US 6,722,360 B2
(45) Date of Patent: Apr. 20, 2004

(54) METHODS AND DEVICES FOR IMPROVING BREATHING IN PATIENTS WITH PULMONARY DISEASE

(76) Inventor: Rajiv Doshi, P.O. Box 18607, Stanford, CA (US) 94309

( * ) Notice: Subject to any disclaimer, the term of this patent is extended or adjusted under 35 U.S.C. 154(b) by 0 days.

(21) Appl. No.: 09/881,862

(22) Filed: Jun. 14, 2001

(65) Prior Publication Data

US 2001/0052344 A1 Dec. 20, 2001

Related U.S. Application Data

(60) Provisional application No. 60/211,990, filed on Jun. 16, 2000.

(51) Int. Cl.⁷ ............................................. A61M 16/00
(52) U.S. Cl. ............................ 128/200.24; 128/207.16; 623/9
(58) Field of Search ..................... 128/207.14, 207.16, 128/200.26, 859, 860, 861, 862, 200.24; 623/9, 11.11, 14.11, 2.21, 2.2; 600/540, 532, 538, 539

(56) References Cited

U.S. PATENT DOCUMENTS

| | | |
|---|---|---|
| 3,370,305 A | 2/1968 | Goott et al. |
| 4,040,428 A | 8/1977 | Clifford |
| RE31,040 E | 9/1982 | Possis |
| 4,403,616 A * | 9/1983 | King ........................ 600/538 |
| 4,456,016 A * | 6/1984 | Nowacki et al. ............ 600/538 |
| 4,533,137 A * | 8/1985 | Sonne ........................ 482/13 |
| 4,582,058 A | 4/1986 | Depel et al. |
| 4,601,465 A | 7/1986 | Roy |

(List continued on next page.)

FOREIGN PATENT DOCUMENTS

| | | |
|---|---|---|
| EP | 1157663 | 11/2001 |
| GB | 2 324 729 | 4/1998 |
| WO | WO 01/002042 | 1/2001 |
| WO | WO 01/013839 | 3/2001 |
| WO | WO 01/013908 | 3/2001 |
| WO | WO 01/087170 | 11/2001 |
| WO | WO 02/038038 | 5/2002 |
| WO | WO 03/022124 | 3/2003 |
| WO | WO 03/034927 | 5/2003 |

OTHER PUBLICATIONS

Dillard et al., "Evaluation of a Novel Intra-bronchial Valve Device to Produce Lung Volume Reduction," Spiration Inc., Redmond, WA., USA—Poster shown at conference in Jun. 2002.

*Primary Examiner*—Aaron J. Lewis
*Assistant Examiner*—Mital Patel
(74) *Attorney, Agent, or Firm*—Knobbe, Martens, Olson & Bear, LLP

(57) ABSTRACT

Methods, apparatus, and kits for enhancing breathing in patients suffering from chronic pulmonary obstructive disease are described. The methods and apparatus rely on increasing flow resistance to expiration in a manner which mimics "pursed lip" breathing which has been found to benefit patients suffering from this disease. In a first example, a device is implanted in a trachea or bronchial passage to increase flow resistance, preferably selectively increase resistance to expiration relative to inspiration. In a second embodiment, a mouthpiece is provided, again to increase resistance to expiration, preferably with a lesser increase in flow resistance to inspiration. In a third embodiment, the patient's trachea or bronchial passage is modified by the application of energy in order to partially close the lumen therethrough.

23 Claims, 6 Drawing Sheets

U.S. PATENT DOCUMENTS

| | | | |
|---|---|---|---|
| 4,822,354 A | | 4/1989 | Elosegui |
| 4,908,028 A | | 3/1990 | Colon et al. |
| 4,973,047 A | | 11/1990 | Norell |
| 4,979,505 A | * | 12/1990 | Cox ............... 128/207.15 |
| 4,984,581 A | | 1/1991 | Stice |
| 5,033,312 A | * | 7/1991 | Stupecky ............ 73/861.53 |
| 5,038,621 A | * | 8/1991 | Stupecky ............ 73/861.53 |
| 5,059,208 A | | 10/1991 | Coe et al. |
| 5,078,739 A | | 1/1992 | Martin |
| 5,092,781 A | | 3/1992 | Casciotti et al. |
| 5,197,980 A | | 3/1993 | Gorshkov et al. |
| 5,255,687 A | | 10/1993 | McKenna |
| 5,383,470 A | * | 1/1995 | Kolbly ................ 600/538 |
| 5,391,205 A | * | 2/1995 | Knight .................... 623/9 |
| 5,415,660 A | | 5/1995 | Campbell et al. |
| 5,459,544 A | | 10/1995 | Emura |
| 5,562,641 A | | 10/1996 | Flomenblit et al. |
| 5,607,469 A | | 3/1997 | Frey |
| 5,763,979 A | | 6/1998 | Mukherjee et al. |
| 5,782,896 A | | 7/1998 | Chen et al. |
| 5,797,920 A | | 8/1998 | Kim |
| 5,876,434 A | | 3/1999 | Flomenblit et al. |
| 5,911,756 A | | 6/1999 | Debry |
| 5,954,766 A | | 9/1999 | Zadno-Azizi et al. ...... 623/2 |
| 5,957,978 A | | 9/1999 | Blom |
| 6,083,141 A | * | 7/2000 | Hougen ............ 128/202.16 |
| 6,258,100 B1 | * | 7/2001 | Alferness et al. ....... 606/108 |
| 6,287,290 B1 | | 9/2001 | Perkins et al. .......... 604/516 |
| 6,293,951 B1 | | 9/2001 | Alferness et al. ....... 606/108 |
| 6,398,775 B1 | | 6/2002 | Perkins et al. .......... 604/514 |
| 6,439,233 B1 | | 8/2002 | Geertsema ......... 128/207.16 |
| 6,510,846 B1 | | 1/2003 | O'Rourke |
| 6,527,761 B1 | | 3/2003 | Buch et al. ............ 604/516 |
| 6,568,387 B2 | | 5/2003 | Davenport et al. .... 128/200.24 |
| 6,585,639 B1 | | 7/2003 | Kotmel et al. ......... 600/116 |
| 6,592,594 B2 | | 7/2003 | Rimbaugh et al. ...... 606/108 |
| 2001/0037808 A1 | | 11/2001 | Deem et al. ....... 128/200.24 |
| 2001/0051799 A1 | | 12/2001 | Ingenito ............... 604/516 |
| 2001/0056274 A1 | | 12/2001 | Perkins et al. .......... 604/516 |
| 2002/0062120 A1 | | 5/2002 | Perkins et al. .......... 604/516 |
| 2002/0077593 A1 | | 6/2002 | Perkins et al. ......... 604/96.01 |
| 2002/0112729 A1 | | 8/2002 | DeVore et al. ....... 128/207.15 |
| 2003/0024527 A1 | | 2/2003 | Ginn ................ 128/200.24 |
| 2003/0050648 A1 | | 3/2003 | Alferness et al. ....... 606/108 |
| 2003/0070682 A1 | | 4/2003 | Wilson et al. ....... 128/207.16 |
| 2003/0083671 A1 | | 5/2003 | Rimbaugh et al. ...... 606/108 |
| 2003/0154988 A1 | | 8/2003 | DeVore et al. ....... 128/207.15 |
| 2003/0158515 A1 | | 8/2003 | Gonzalez et al. ...... 604/93.01 |

* cited by examiner

METHODS AND DEVICES FOR IMPROVING BREATHING IN PATIENTS WITH PULMONARY DISEASE

RELATED APPLICATION

This is a continuation-in-part of provisional U.S. patent application Ser. No. 60/211,990, filed Jun. 16, 2000.

BACKGROUND OF THE INVENTION

The present invention relates generally to the field of pulmonology, and more particularly to the field of chronic obstructive pulmonary disease. In this regard, the invention provides devices and methods that are useful in improving breathing in patients with chronic pulmonary disease.

Chronic obstructive pulmonary diseases (COPD) is both very common and increasing in incidence. COPD is the fourth most common cause of death in this country and the morbidity and mortality it causes continue to increase.

COPD comprises chronic bronchitis and emphysema. In both chronic bronchitis and emphysema, airflow obstruction limits the patient's air flow during exhalation. COPD is a progressive disease characterized by worsening baseline breathing status over a period of many years with sporadic exacerbations often requiring hospitalization.

Typically, patients with COPD have extensive smoking histories; smoking is the major risk factor for development of COPD. Symptoms typically begin in the fifth decade of life with progression to dyspnea on exertion during the sixth and seventh decade. Early symptoms include increasing sputum production, and sporadic acute exacerbations characterized by increased cough, purulent sputum, wheezing, dyspnea, and fever. As the disease progresses, the acute exacerbations become more frequent. Late in the course of the disease, the patient may develop hypercapnea, hypoxemia, erythrocytosis, cor pulmonale with right heart failure, and edema.

Though both chronic bronchitis and emphysema lead to chronic obstruction leading to limitation in expiratory flow, the pathophysiology and clinical presentation of each disease are different. Chronic bronchitis is characterized by chronic cough with sputum production leading to obstructed expiration. Pathologically, there is mucosal and submucosal edema and inflammation and an increase in the number and size of mucus glands. Emphysema is characterized by destruction of the lung parenchyma leading to loss of elastic recoil, reduced tethering of airways, and obstruction to expiration. Pathologically, the distal airspaces are enlarged.

Management of COPD is largely medical and infrequently surgical. Initially, exercise and smoking cessation are encouraged. Medications including bronchodilators (including beta-agonists, anti-cholinergics, and theophylline) and anti-inflammatories are routinely prescribed but are by no means curative. Pulmonary rehabilitation is often prescribed and has been shown to improve quality of life and sense of well being. Long term oxygen is generally reserved for the more severely affected patients. Surgical options are limited and include lung volume reduction surgery and lung transplantation. Both of these surgical options, because of associated morbidity, are infrequently performed.

One of the important components of the aforementioned pulmonary rehabilitation is breathing retraining. This involves teaching the patient new breathing techniques that reduce hyperinflation of the lungs and relieve expiratory airflow obstruction. One of the goals is of course to reduce the level of dyspnea. Typically, these new breathing techniques include diaphragmatic and pursed-lip breathing. This latter technique, pursed-lip breathing, involves inhaling slowly through the nose and exhaling through pursed-lips (as if one were whistling), taking twice as long to exhale as to inhale. Most COPD patients instinctively learn how to perform pursed-lip breathing in order to relieve their dyspnea.

The belief among the medical community is that by producing a proximal obstruction (pursing the lips), the effect is to splint open the distal airways that have lost their tethering. In other words, the affected airways that would normally collapse upon themselves remain open when the patient breathes through pursed-lips.

Medical literature has confirmed the utility of pursed-lip breathing in COPD patients. Specifically, it has been found that respiratory rate is reduced, tidal volumes are increased, and oxygen saturation is improved. All of these contribute to improved dyspnea on the part of the patient. The drawbacks of pursed-lip breathing are twofold. First, because it requires conscious effort, the patient cannot breath through pursed lips while sleeping. As a result, the patient can still become hypoxic at night and may develop pulmonary hypertension and other sequelae as a result. Second, since the patient has to constantly regulate his own breathing, this interferes with his performing other activities.

Clearly, there is a need for a medical device and/or procedure that mimics the effect of pursed-lip breathing without suffering from the above drawbacks. As such, there is much interest in the development of new medical devices and methods for use in procedures for patients with COPD.

SUMMARY OF THE INVENTION

According to the present invention, there is a potentially significant benefit for a patient who undergoes a simple procedure that creates an obstruction to expiratory airflow within the airways. There are several possible means of achieving the requisite expiratory obstruction. A device capable of delivering energy (radiofrequency, ultrasound, microwave, laser, cryo) could be used to create a localized scarring or area or stenosis in the appropriate location, most likely in the trachea, main bronchi, or other conducting airways. The goal of this treatment would be to create a proximal obstruction that would alleviate the expiratory limitations caused by the collapse of the smaller distal airways. In COPD, inspiratory airflow is relatively unaffected, so the presence of a fixed obstruction present during both phases of the respiratory cycle would not likely obstruct inspiratory airflow to an appreciable amount.

Another approach would be to implant a device into the airways (most likely the trachea or bronchi) that would create a similar obstruction. This device could either be composed of non-moving parts, or could partially obstruct the airway on expiration and not obstruct the airway on inspiration. That is, the direction of the airflow would determine if the obstruction were present.

Such a device and or methods will mimic the positive benefits of pursed-lip breathing, specifically the increase in tidal volume, decrease in respiratory rate, increase in oxygen saturation, and improvement in patient dyspnea.

In a first aspect, the present invention will provide implantable devices for use in the treatment of COPD. The implantable devices will usually comprise a frame which is implantable within a lung passageway, typically the trachea or a bronchial passage. The frame will include a mechanism or other means for increasing flow resistance to expiration.

In a simple embodiment, the flow resistance means will be a simple flow resistor that provides increased resistance to both inspiration and expiration. In such cases, the flow resistor could be a simple plate which is held within the lung passage and which occludes some portion of the luminal cross-sectional area. Preferably, however, the means will comprise a flow resistor which selectively increases resistance to expiration while minimally increasing flow resistance to inspiration. It will be appreciated that the frame could carry a variety of "one-way valve structures," or other flow responsive elements which open to inspiration and close to expiration. Of course, when closing to expiration, the means should not fully occlude the lung passage since the patient must still be able to exhale, albeit at a slower rate in order to assure a more complete evacuation of the lungs.

In a second aspect, the present invention comprises a mouthpiece which a user may conveniently insert and remove depending on need. The mouthpiece will be adapted to fit in the mouth, typically being held between the teeth in the upper and lower jaws. As with the earlier embodiment, the mouthpiece embodiment will increase flow resistance to expiration. Usually, there will be a much lesser increase in resistance to inspiration, although the presence of the mouthpiece will very likely lead to at least a minimal increase in flow resistance to inspiration. In the preferred embodiments, a variety of one-way valves, flaps, or other flow-responsive elements may be provided.

In a third aspect, the present invention provides methods for treating patients suffering from chronic obstructive pulmonary disease (COPD). The methods broadly comprise creating a resistance to expiratory flow in a lung passage, typically the trachea or a bronchial passage. The methods may comprise use of any of the devices desribed above. For example, the flow resistance may be created by implanting a flow resistor, either one with a fixed flow resistance or one with a variable flow resistance, i.e., which is higher to expiration than inspiration. Alternatively, the flow resistance could be increased by modifying a lung passage to decrease the available luminal area. Such methods will typically comprise applying energy to a portion of the luminal wall, typically in the trachea or bronchial passage, so that the lumen decreases in response to the application of energy. In a first specific instance, the energy can be applied in such a way that the wall is injured and scar tissue forms to partially occlude the passage. In a second instance, the energy can be applied under conditions which shrink the collagen in order to close the passage, but where minimal tissue damage and injury response occur.

DESCRIPTION OF THE SPECIFIC EMBODIMENTS

Figure 1:
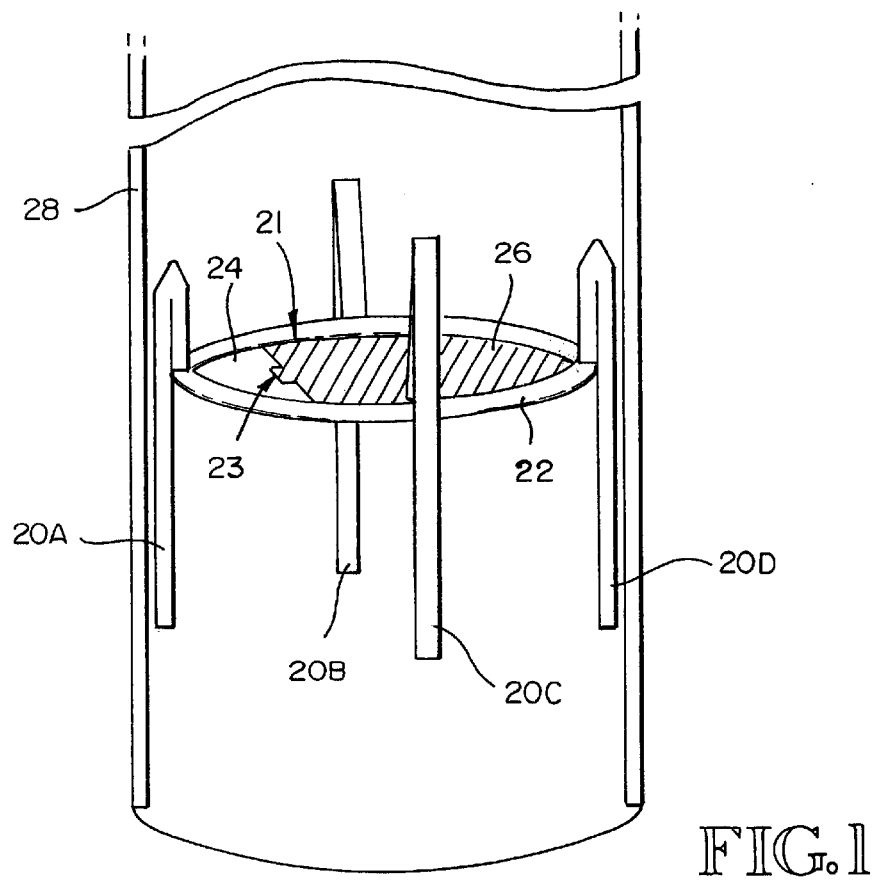
FIG. 1 provides a three-dimensional view of a first embodiment of the subject devices where the device is depicted in a first, retracted position.

Medical devices and methods for their use in improving breathing in COPD patients are provided.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It must be noted that as used in this specification and the appended claims, the singular forms "a," "an," and "the" include plural reference unless the context clearly dictates otherwise. Unless defined otherwise all technical and scientific terms used herein have the same meaning as commonly understood to one of ordinary skill in the art to which this invention belongs.

Devices

As summarized above, the subject devices are devices for use in improving the breathing of patients with chronic obstructive pulmonary disease. As such, the subject devices are devices designed to alter the air flow into and out of the lungs. A feature of the subject devices is that they contain a means of obstructing air flow, specifically air flow during the expiratory phase of the respiratory cycle.

As such, the subject devices consist of two main components, the first is a means of anchoring the device to a certain location, the second a means of regulating gas flow to and from the lungs.

In those embodiments where the anchoring means is by a plurality of expanding anchoring legs, these anchoring legs secure the device temporarily or permanently in the trachea or bronchi. These legs may be made of a large number of materials, with the preference that the chosen material have shape memory. That is, the legs would be expected to spring outward following deployment and thereby facilitate contact with the surrounding tissues such as the trachea, bronchi, and other respiratory conduits.

In those embodiments where the anchoring means is a removable mouthpiece, the contour of the mouthpiece fits securely into the teeth and/or soft palate of the user, allowing the user to insert or remove the device as needed.

Another feature that is present in many embodiments in the use of a novel valve that does not appreciably impede air flow in a certain direction (inspiration), and partially impedes air flow in the other direction (expiration). Moreover, the valvular mechanism in many embodiments allows for the expiratory obstruction to be relieved if a certain degree of air flow or pressure differential across the device is achieved, as might be the case with coughing. For example, in some embodiments, the valve flap is made of a shape memory material that is bendable; when the pressure differential across the valve or expiratory air flow is large enough, the flap bends upon itself thereby relieving the obstruction. This is important during coughing and also facilitates the clearance of mucous and other substances during coughing. After the cough, the flap returns to its original, non-bent conformation.

In certain embodiments, the subject devices include a shape memory element or elements, both for use in anchoring the device within the body or in the valvular mechanism itself. Any convenient shape memory material which provides for the requisite features of flexibility and resumption of configuration following removal of applied force may be employed in these embodiments. As such, shape memory alloys find use. A variety of shape memory alloys are known, including those described in U.S. Pat. Nos.: 5,876,434; 5,797,920; 5,782,896; 5,763,979; 5,562,641; 5,459,544; 5,415,660; 5,092,781; 4,984,581; the disclosures of which are herein incorporated by reference. The shape memory alloy that is employed should generally be a biocompatible alloy. Specific biocompatible alloys that find use include those nickel-titanium (NiTi) shape memory alloys sold under the Nitinol™ name by Memry Corporation (Brookfield, Conn.). Also of interest are spring steel and shape memory polymeric or plastic materials, where such materials include polypropylene, polyethylene, etc.

The subject devices may be manufactured using any convenient protocol, where suitable protocols are known in the art. Representative manufacturing methods that may be employed include machining, and the like.

Turning now to the figures, FIG. 1 provides a three-dimensional view of a first embodiment of the subject devices in which the device is implantable, where the device is depicted in a first, retracted position. The device shown in FIG. 1 has multiple anchoring members 20A, 20B, 20C, and 20D. Located centrally to the anchoring members 20A, 20B, 20C, and 20D, is a central rim 22. A planar element 24, fixed to the central rim 22, is connected to a movable element 26 by hinge joint 23 to form a central valve 21. The entire device, in the retracted position, is housed within a catheter 28 which allow the device to be placed at the appropriate location within the respiratory tract prior to deployment.

Figure 2:
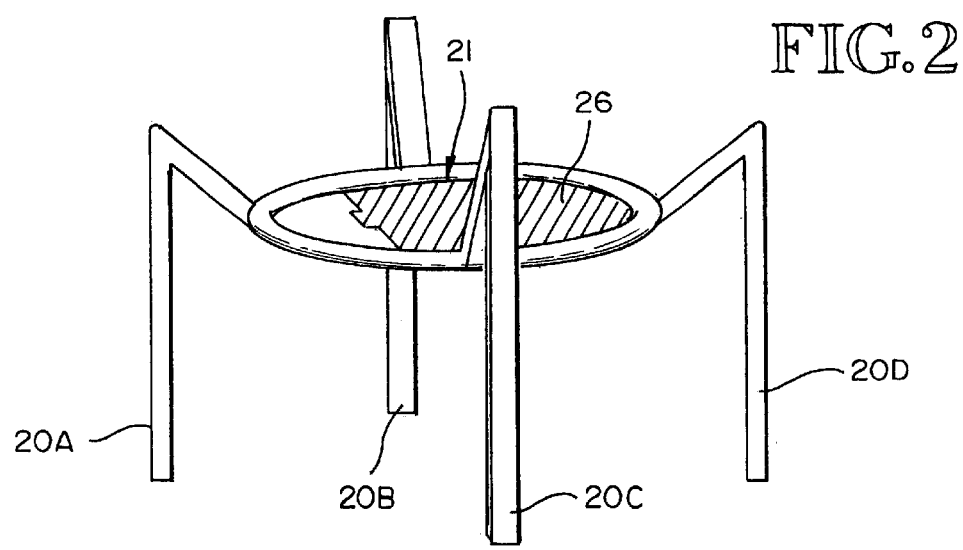
FIG. 2 provides a three-dimensional view of the device shown in FIG. 1, where the device is depicted in the deployed position with closure of the central valve.

FIG. 2 provides a three-dimensional view of the device shown in FIG. 1, where the device is depicted in the deployed position with closure of the central valve 21. Anchoring members 20A, 20B, 20C, and 20D are in the deployed or non-retracted position which allows the device to be anchored to the surrounding tissues (not shown). Moveable element 26 is in the closed position because of the flow of air from distal to proximal airways as might be expected during exhalation.

Figure 3:
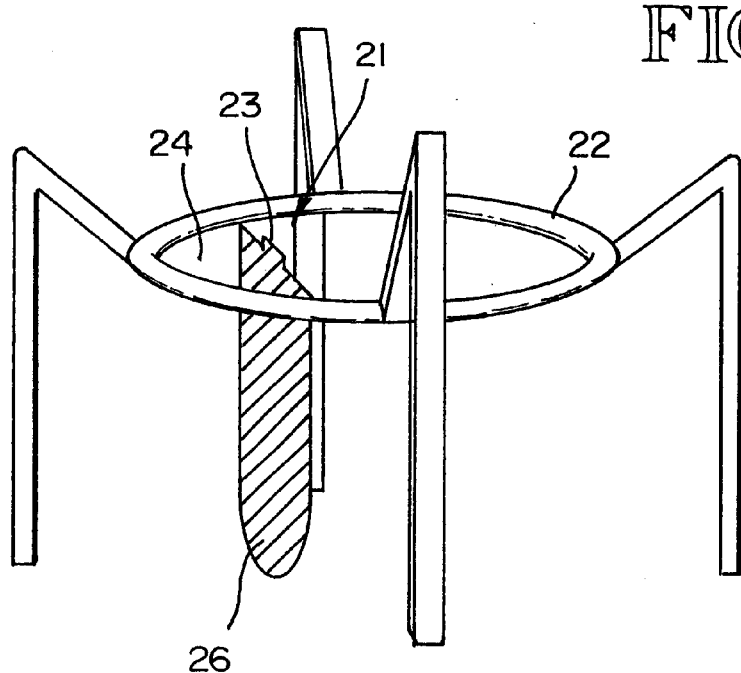
FIG. 3 provides a three-dimensional view of the device shown in FIG. 1, where the device is depicted in deployed position with opening of the central valve in the downward direction.

FIG. 3 provides a three-dimensional view of the device shown in FIG. 1, where the device is depicted in deployed position with complete opening of the central valve 21 in the downward direction. The moveable element 26 pivots around the hinge joint 23 resulting in an opening through the center of the device. This pivoting is due to the flow of air from the proximal to distal airways as expected during inhalation. Fixed element 24 does not move during this pivoting; it remains attached to rim 22.

Figure 4:
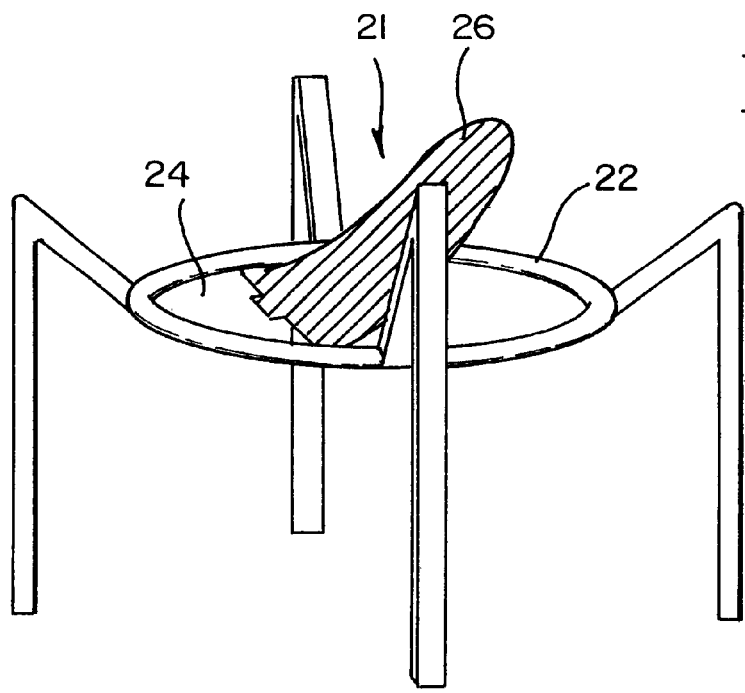
FIG. 4 provides a three-dimensional view of the device shown in FIG. 1, where the device is depicted in a deployed position with deflection of the central valve in the upwards direction.

FIG. 4 provides a three-dimensional view of the device shown in FIG. 1, where the device is depicted in a deployed position with deflection of the central valve 21 in the upwards direction for partial opening. The moveable element 26 has been transiently bent by the large air flow from the distal to proximal airways at high pressure exceeding that of normal expiration as might be expected during a cough. Moveable element 26 returns to its position in FIGS. 2 and 3 during subsequent stages of the regulatory cycle.

Figure 5:
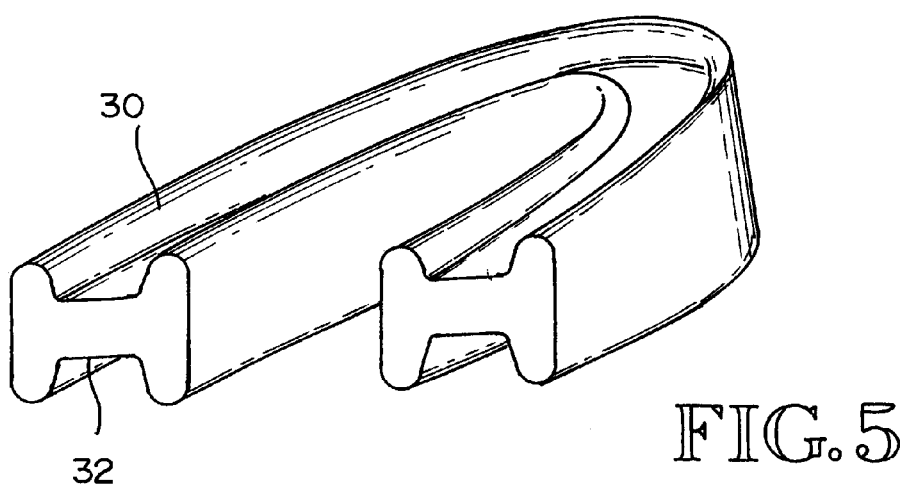
FIG. 5 provides a three-dimensional view of a second embodiment of the subject devices in which the device is removable and fits within the oral cavity.

FIG. 5 provides a three-dimensional view of a second embodiment of the subject devices in which the device is removable and fits within the oral cavity. In this embodiment, indentations 30 and 32 are grooves in which the user's teeth and/or gums fit, serving as a means to secure the device within the oral cavity.

Figure 6:
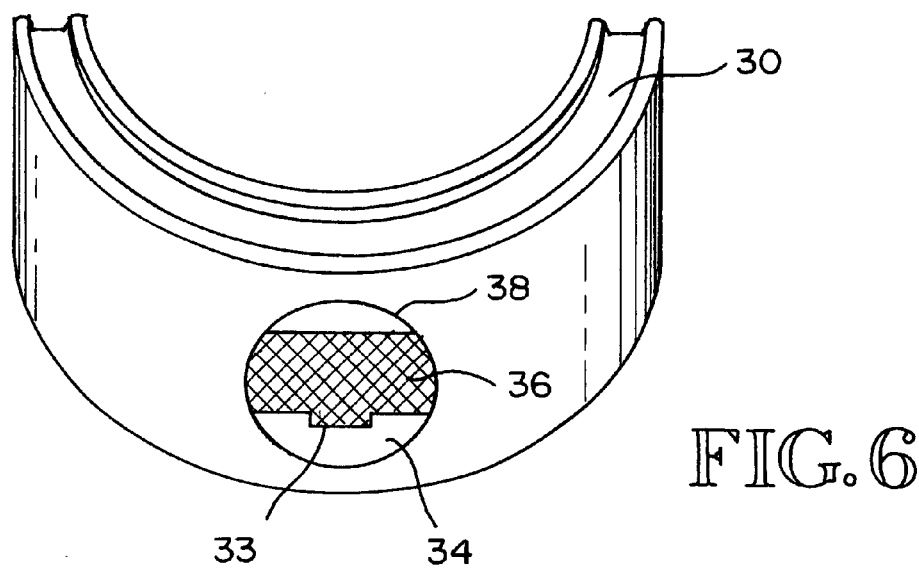
FIG. 6 provides a three-dimensional view of the device shown in FIG. 5, where the device is depicted during exhalation with closure of the valve.

FIG. 6 provides a three-dimensional view of the device shown in FIG. 5, where the device is depicted during exhalation with closure of the valve. Moveable element 36 is in the closed position and is attached to fixed element 34 via hinge 33. Fixed element 34 is also permanently attached to rim 38.

Figure 7:
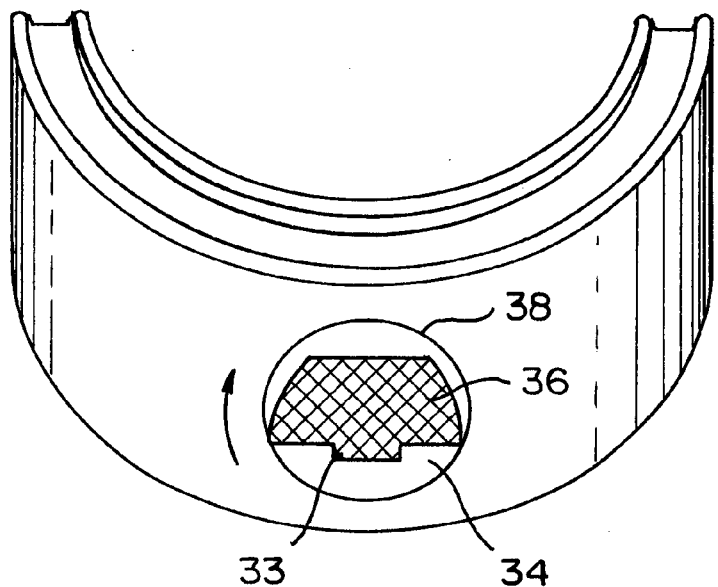
FIG. 7 provides a three-dimensional view of the device shown in FIG. 5, where the device is depicted during inhalation with inward opening of the valve.

FIG. 7 provides a three-dimensional view of the device shown in FIG. 5, where the device is depicted during inhalation with inward opening of the valve, with inward opening of the moveable element 36.

Figure 8:
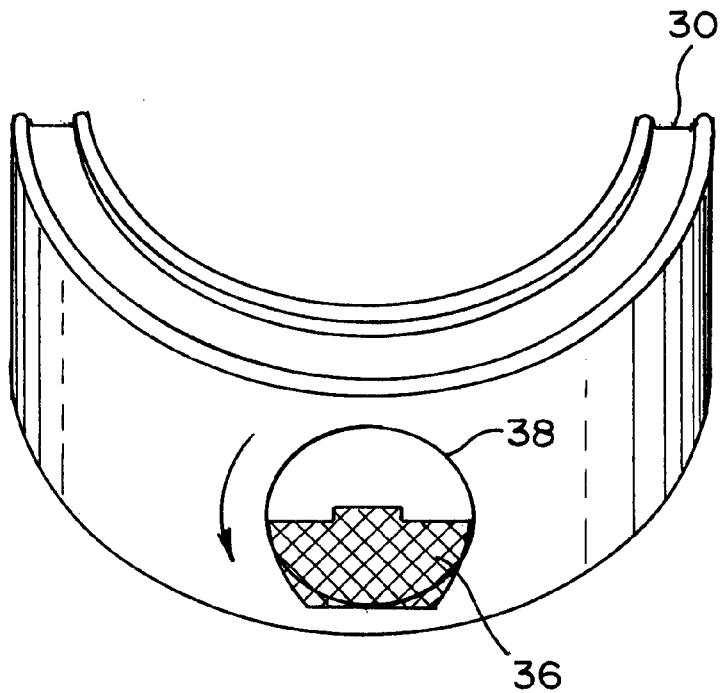
FIG. 8 provides a three-dimensional view of the device shown in FIG. 5, where the device is depicted with outward deflection of the valve.
Figure 9:
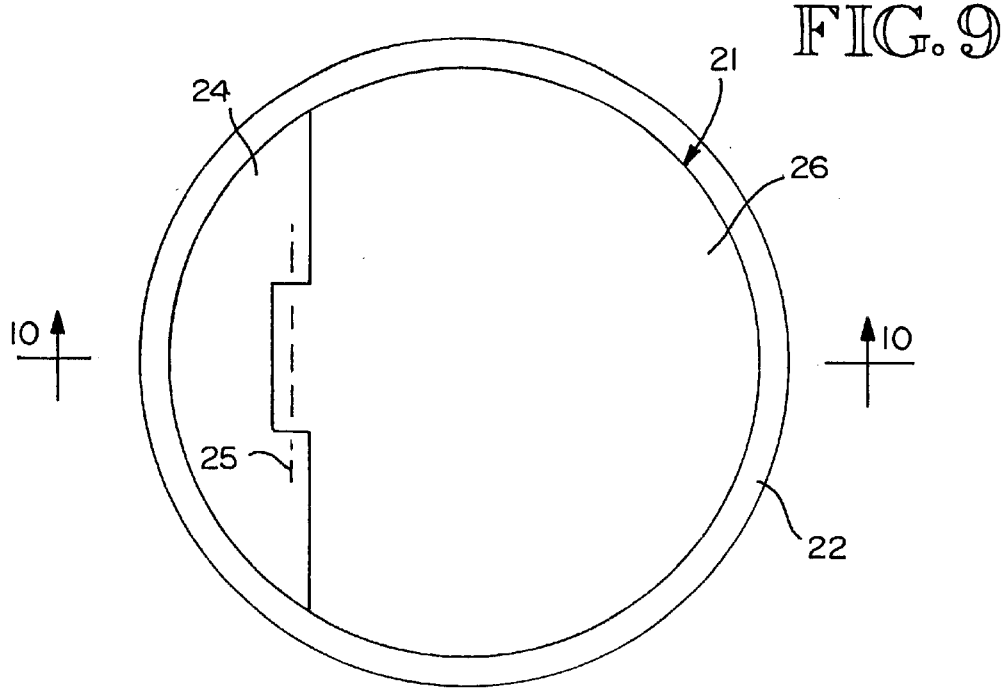
FIG. 9 is a top plan view of the rim and valve of FIGS. 1–4.
Figure 10:
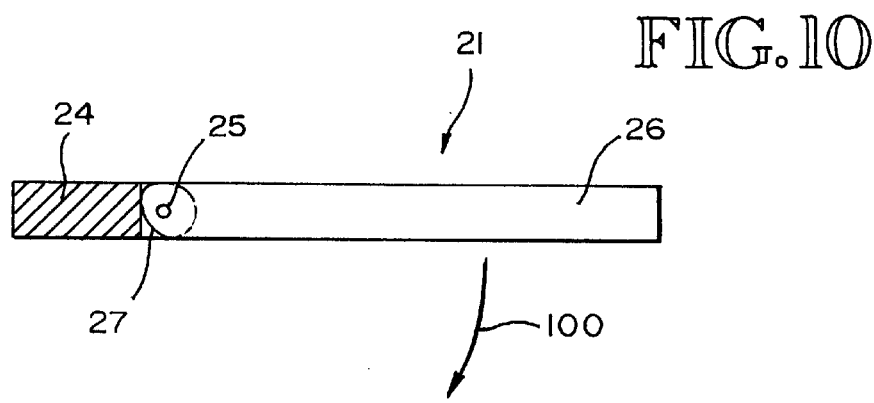
FIG. 10 is a cross-sectional view of the valve taken along lines 10—10 of FIG. 9.

FIG. 8 provides a three-dimensional view of the device shown in FIG. 5, where the device is depicted with outward deflection of the valve. This might occur during a cough, during which moveable element 36 bends outward in response to increased air flow and/or increase pressure gradient across the length of the device.

Figure 11:
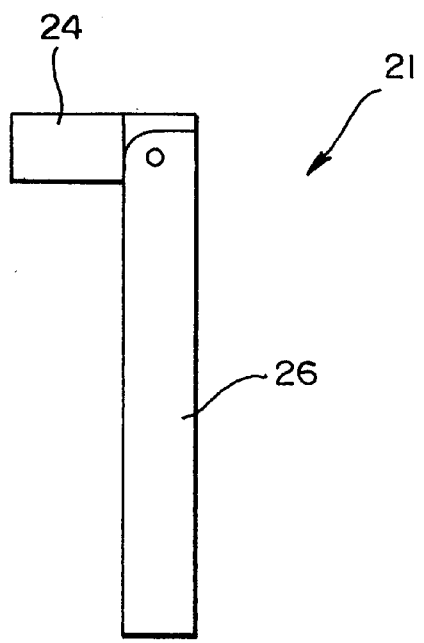
FIG. 11 is a side view of the valve when in a fully opened condition responsive to inspiration.

FIGS. 9–12 provide more detailed views of the operation of the valve 21. The moveable element 26 is hingedly coupled to the fixed element 24 by a hinge pin 25. The moveable element 26 further has a cam surface 27 permitting the moveable element 26 to freely move in the direction of arrow 100 during inspiration. This condition of the valve 21 is shown in FIG. 11. During normal expiration, the moveable element 26 returns to the closed position illustrated in FIG. 10.

Figure 12:
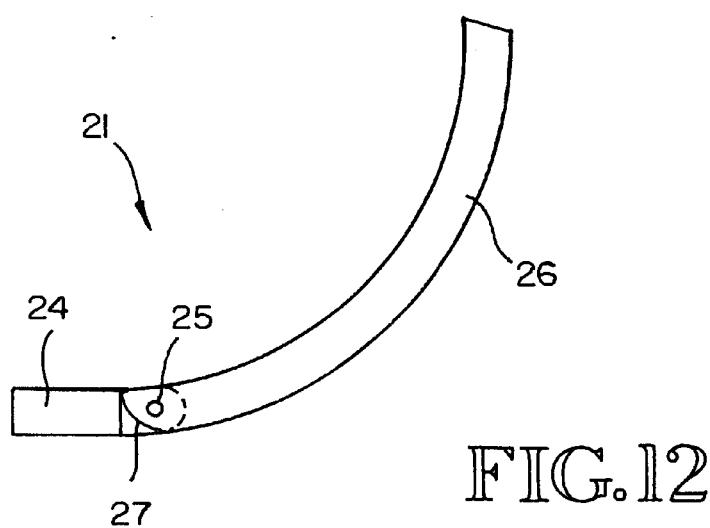
FIG. 12 is a side view of the valve when in a partially opened condition responsive to expiration of high pressure.

During expiration at high pressure, such as during a cough, the hinged end of the moveable element 26 remains fixed due to the cam surface 27. However, the moveable element 26 is permitted to flex along its length as shown in FIG. 12 to partially open. After the cough subsides, the moveable element 26 then returns to a condition commensurate with the inspiration or normal expiration of the patient.

Hence, the valve provides a first flow resistance to airflow from proximal airways to distal airways (inhalation) and a second flow resistance to normal expiration air flow from distal airways to proximal airways. In addition, the valve further provides a third flow resistance to high pressure expiration air flow from distal airways to proximal airways. The first airflow resistance is less than the third air flow resistance and the third air flow resistance is less than the second airflow resistance. As a result, normal inspiration, normal expiration, and high pressure expiration are accommodated while maintaining improvement in the breathing of the patient.

Utility

The subject methods and devices find use with a variety of different types of animals. Representative animals with which the subject methods and devices find use include, but are not limited to: canines; felines; equines; bovines; ovines; etc. and primates, particularly humans.

Kits

Also provided are kits that at least include the subject devices. The subject kits at least include a device of the subject invention and instructions for how to use the device in a procedure. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. The instructions may take any form, including complete instructions for how to use the device or as a website address with which instructions posted on the world wide web may be accessed.

The following examples are offered by way of illustration and not by way of limitation.

EXPERIMENTAL

I. Use of the Device

A. Implantable Application:

Using standard visualization techniques including but not limited to flexible and rigid bronchoscopy, laryngoscopy, fluoroscopy, and direct vision (as in open surgery), a catheter or other similar device capable of housing the device is directed to appropriate site within the pulmonary tree (trachea, bronchi, or bronchioles). The device shown in FIG. 1 shows the retracted (more compact) version of the device which fits within the distal segment of the catheter or housing. At the appropriate site, the device is released, most likely using a plunger to keep the device stationary as the protective housing is advanced proximally. Once out of the housing, the anchoring elements 20A, 20B, 20C, and 20D spring to their preferred shape. This preferred shape is one in which the anchoring elements are positioned away from each other and are in contact with the respiratory conduit, thus securing the device in place.

Once deployed, the device works as follows. During inspiration, the device remains in the open position. Open position means the moveable element 26 has pivoted around hinge 23 towards the direction of the distal airways. This pivoting action is the result of the airflow from the proximal to distal airways. During exhalation, the airflow from the distal airways to the proximal airways results in the moveable element 26 pivoting in the opposite direction to a closed position in which the moveable element 26 is adjacent to rim 22. This creates the requisite expiratory obstruction. During a cough, the significantly increased flow of air from the distal to the proximal airways causes the moveable element 26 to deflect upon itself with no additional pivoting around hinge 23 as compared to normal exhalation. This mechanism serves to relieve the expiratory obstruction and promotes clearance of secretion and debris.

B. Removable Application:

The device shown in FIGS. 5 and 6 is placed into the subject's mouth by medical personnel or by the subject himself where it is kept in place by the subject's teeth and shape of the oral cavity. The device can be worn at night, during the day, or both.

Once in place, the device works as follows. During inspiration, the device remains in the open position. Open position means the moveable element 36 has pivoted around hinge 33 towards the direction of the distal airways. This pivoting action is the result of the airflow from the proximal to distal airways. During exhalation, the airflow from the distal airways to the proximal airways results in the moveable element 36 pivoting in the opposite direction to a closed position in which the moveable element 36 is adjacent to rim 38. This creates the requisite expiratory obstruction. During a cough, the significantly increased flow of air from the distal to the proximal airways causes the moveable element 36 to deflect upon itself with no additional pivoting around hinge 33 as compared to normal exhalation. This mechanism serves to relieve the expiratory obstruction and promotes clearance of secretion and debris.

It is evident that the subject devices provide a number of important advantages over prior art devices. The subject devices improve the breathing of the patient by mimicking the effects of pursed-lip breathing which is adopted instinctively by affected patients. Physiologically, it is anticipated that the beneficial effects of the device will be the same as those experienced in pursed-lip breathing, specifically improving oxygen saturation, decreasing respiratory rate, and increasing tidal volume. This in turn will reduce the probability of the affected patient developing pulmonary hypertension, right-sided heart failure and other sequelae secondary to chronic obstructive pulmonary disease. Furthermore, the devices offer the significant advantage of freeing the patient from constantly pursing his lips, which is a conscious action. Moreover, in contrast to pursed-lip breathing which requires conscious effort and cannot be performed during sleep, these devices allow pursed-lip breathing throughout the day. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A device for partially occluding an airway in a patient, the device comprising:

a frame having at least one anchoring member and configured to be implanted within a trachea or bronchial passage thereby dividing a lumen of the trachea or bronchial passage into a first portion and a second portion, the frame being further arranged to allow inspiration and expiration air flow through the first portion; and means on the frame for increasing resistance to expiration air flow through the second portion.

2. The device of claim 1 wherein the means selectively increases air flow resistance to expiration while increasing resistance to inspiration to a lesser extent.

3. The device of claim 2 wherein the means comprises a flow responsive element which opens to inspiration and closes to expiration.

4. The device of claim 1 wherein the means comprises a fixed element.

5. A device for enhancing breathing in a patient suffering from chronic obstructive pulmonary disease, the device comprising:

a mouth piece for holding in the patient's mouth; and means on the mouthpiece for causing an air flow resistance to expiration that is greater than an air flow resistance to inspiraton, the inspiration and expiration being along the same air flow pathway.

6. A method for treating patients suffering from chronic obstructive pulmonary disease, the method comprising:

providing flow resistor configured to substantially resist airflow in a first direction past the resistor without entirely occluding airflow in the first direction, the resistor being further configured to substantially allow airflow in a second direction past the resistor;

implanting the flow resistor in a bi-directional airway of a patient in such an orientation that the resistor resists expiratory air flow more than inspiratory air flow.

7. The method of claim 6 wherein providing a flow resistor comprises providing a valve with a movable occluding member.

8. A method for treating patients suffering from chronic obstructive pulmonary disease, the method comprising:

implantably creating a resistance in a tracheal or bronchial passage to a portion of expiratory air flow by implanting a flow resistor in the trachea or bronchial passage; wherein the flow resistor comprises an implantable frame and means on the frame for selectively increasing flow resistance to expiration.

9. A method for treating patients suffering from chronic obstructive pulmonary disease, the method comprising:

creating a resistance in a tracheal or bronchial passage to a portion of expiratory air flow by applying energy to a portion of the tracheal or bronchial passage to alter a section of tissue in the passage to partially occlude the lumen of the passage.

10. A device that partially occludes an airway in a patient, the device including:

an air flow element having at least one anchoring member and configured for implantation within an airway including at least one of a trachea and a bronchus, wherein the airway is divided into a first portion and a second portion by the device;

the air flow element further having an air flow pathway that allows inspiration and expiration air flow through the first portion and an air flow resistance element that resists expiration air flow through the second portion.

11. The device of claim 10 wherein the air flow resistance element provides a first flow resistance to inspiration and a second flow resistance to expiration, the second flow resistance being greater than the first flow resistance.

12. The device of claim 10 wherein the air flow resistance element comprises a valve.

13. The device of claim 12 further including a frame that supports the valve.

14. The device of claim 10 wherein the air flow resistance element provides a first flow resistance to air flow from proximal airways to distal airways, a second flow resistance to first air flow from distal airways to proximal airways, and a third flow resistance to second air flow from distal airways to proximal airways, wherein the second flow resistance is greater than the third flow resistance and the second airflow from distal airways to proximal airways is greater than the first airflow from distal airways to proximal airways.

15. The device of claim 14 wherein the third air flow resistance is greater than the first air flow resistance.

16. A device for partially occluding an airway in a patient, the device comprising:

a frame configured to be implanted within an airway of a patient, said frame dividing said airway into a first portion and a second portion, wherein the frame is configured to allow both inspiratory and expiratory air to flow past the frame in the first portion, and wherein the frame comprises an airflow-impeding member configured to increase resistance to expiratory airflow through the second portion.

17. The device of claim 16, wherein the frame comprises an anchor member configured to engage an airway wall to retain the device against movement within the airway.

18. The device of claim 17, wherein the first portion comprises an area between the airflow-impeding member and the airway wall.

19. The device of claim 16, wherein the airflow-impeding member is configured to allow inspiratory airflow to flow through the second portion substantially unimpeded.

20. The device of claim 19, wherein the airflow-impeding member comprises a hinged flap.

21. A device for increasing resistance to expiratory airflow in a patient, the device comprising:

a frame configured to be implanted within a trachea or a bronchial passageway of a patient, the frame comprising an airflow-restricting member, wherein the airflow restricting member is configured to create a first resistance to expiratory airflow that is substantially greater than a resistance to inspiratory airflow.

22. The device of claim 21, wherein the resistance to inspiratory airflow is substantially negligible in relation to the resistance to expiratory airflow.

23. The device of claim 21, wherein the airflow-restricting member is further configured to create a second resistance to expiratory airflow when an expiratory air pressure exceeds a threshold value, the second resistance to expiratory airflow being less than said first resistance to expiratory airflow.

* * * * *